Figure 1:
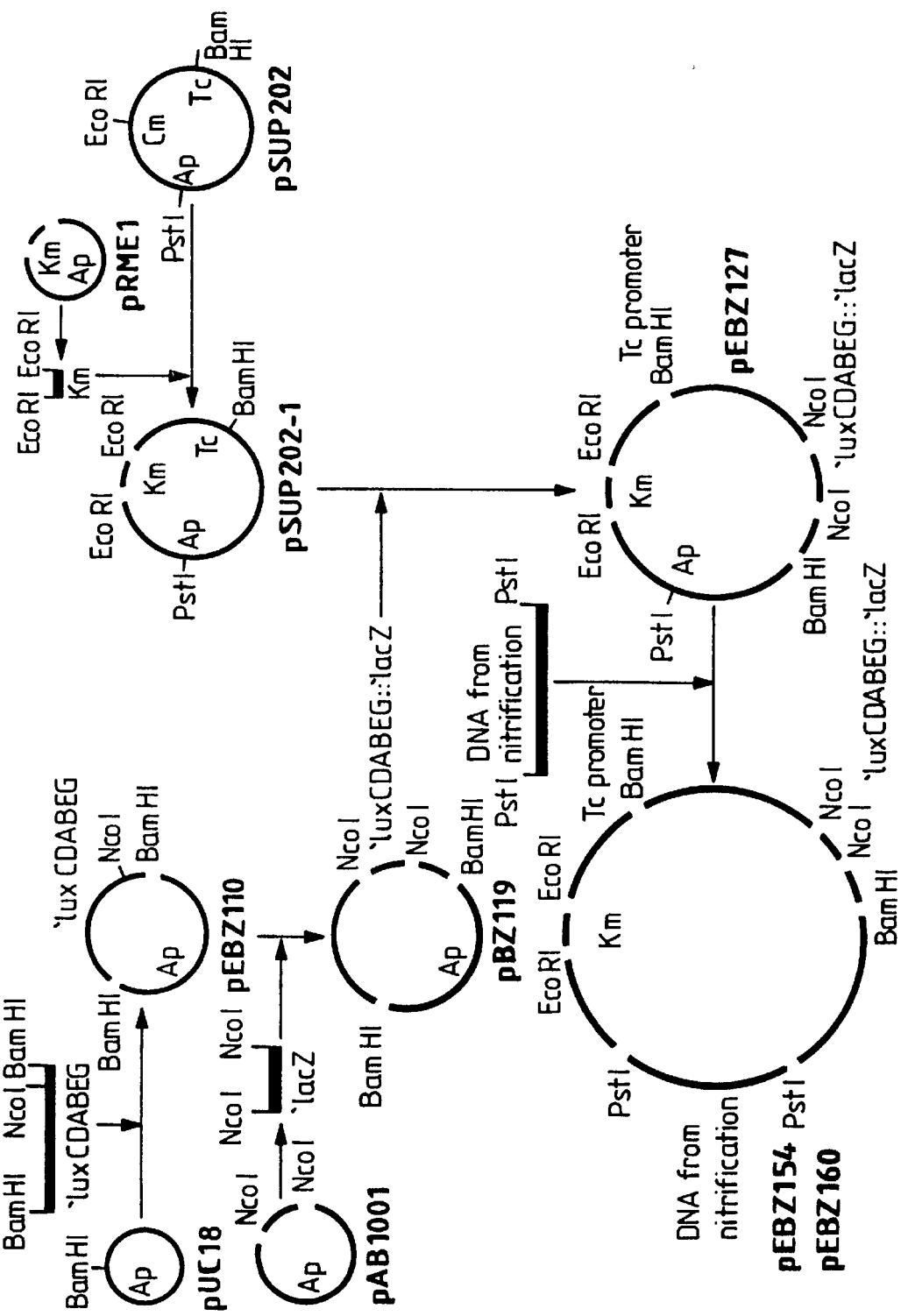

United States Patent [19]

Eberz et al.

[11] Patent Number: 5,900,362
[45] Date of Patent: May 4, 1999

[54] LUMINESCENT NITRIFYING MICROORGANISMS

[75] Inventors: Günther Eberz, Leverkusen; Hans-Georg Rast, Bergisch Gladbach, both of Germany

[73] Assignee: Bayer Aktiengesellschaft, Leverkusen, Germany

[21] Appl. No.: 08/522,765

[22] Filed: Sep. 1, 1995

[30] Foreign Application Priority Data

Sep. 8, 1994 [DE] Germany ............................. 44 31 964

[51] Int. Cl.⁶ .............................. C12Q 1/12; C12N 15/66; C12N 1/21
[52] U.S. Cl. ...................... 435/37; 435/172.1; 435/252.3
[58] Field of Search .............................. 435/172.1, 252.3, 435/37

[56] References Cited

U.S. PATENT DOCUMENTS

| | | | |
|---|---|---|---|
| 4,626,504 | 12/1986 | Puhler et al. | 435/172.3 |
| 4,861,709 | 8/1989 | Ulitzur et al. | 435/6 |
| 5,186,800 | 2/1993 | Dower | 204/180.1 |

FOREIGN PATENT DOCUMENTS 3833628   4/1990   Germany .

OTHER PUBLICATIONS

Bulich, A.A. et al. "The use of luminescent bacteria for biological monitoring of water quality" Proceedings of International Symposium Analytical Applied Bioluminescence and Chemiluminescence (1979), Schram, E. et al. (Ed), pp. 193–211, abstract.

Sayavedra–Soto, L.A. et al. "Characterization of the gene encoding hydroxylamine oxidoreductase in *Nitrosomonas europaea*" Journal of Bacteriology (Jan. 1994), vol. 176, No. 2, pp. 504–510.

Hommes, N.G. et al. "Mutagenesis of hydroxylamine oxiodoreductase in *Nitromonas europaea* by transformation and recombination" Journal of Bacteriology (Jul. 1996), vol. 178, No. 13, pp. 3710–3714.

E.A. Meighen, Microbiological Reviews, vol. 55, No. 1, pp. 123 –142, (1991).

E.A. Meighen, et al., Advances in Microbial Physiology, vol. 34, pp. 2 –67, (1993).

J. Engebrecht, et al., Proc. Natl. Acad. Sci., vol. 81, pp. 4154 –4158, (1984).

J.M. Collard, et al., FEMS Microbiology Reviews, vol. 14, pp. 405 –414, (1994).

R. Kanne, et al., Fresenius Z. Anal. Chem., vol. 325, pp. 136 –139, (1986).

G. Britton, et al., Reviews of Environmental Contamination and Toxicology, vol. 125, pp. 1 –22, (1992).

BIOSIS–Reference AN 83:242814, (1994).

Parker, C.E. et al. (1984) "Assessment of bacterial ATP response as a measurement of aquatic toxicity" Drug Chem. Toxicol. vol. 1:283–293.

*Primary Examiner*—Kawai Lau
*Attorney, Agent, or Firm*—Sprung Kramer Schaefer & Briscoe

[57] ABSTRACT

The method of producing luminescent bacteria is based on the transfer of genetic information for biological luminescence to obligate chemolithoautotrophic nitrifying microorganisms. In particular, luciferase DNA or a luciferase-beta-galactosidase transcription fusion is transferred into ammonia-oxidizing bacteria with the aid of plasmid- or transposon vector systems. The bioluminescent nitrification microorganisms, particularly Nitrosomonas strains modified by genetic engineering, are used in order to identify specific inhibitors during nitrification processes, the viability of these microorganisms being determined by measuring the decrease in luminescence. A particularly important application is that inhibitors in a nitrifying biological sewage treatment plant can be detected in this manner.

12 Claims, 16 Drawing Sheets

Fig. 1 Production of luciferase-encoding suicide plasmids

Figure 2:
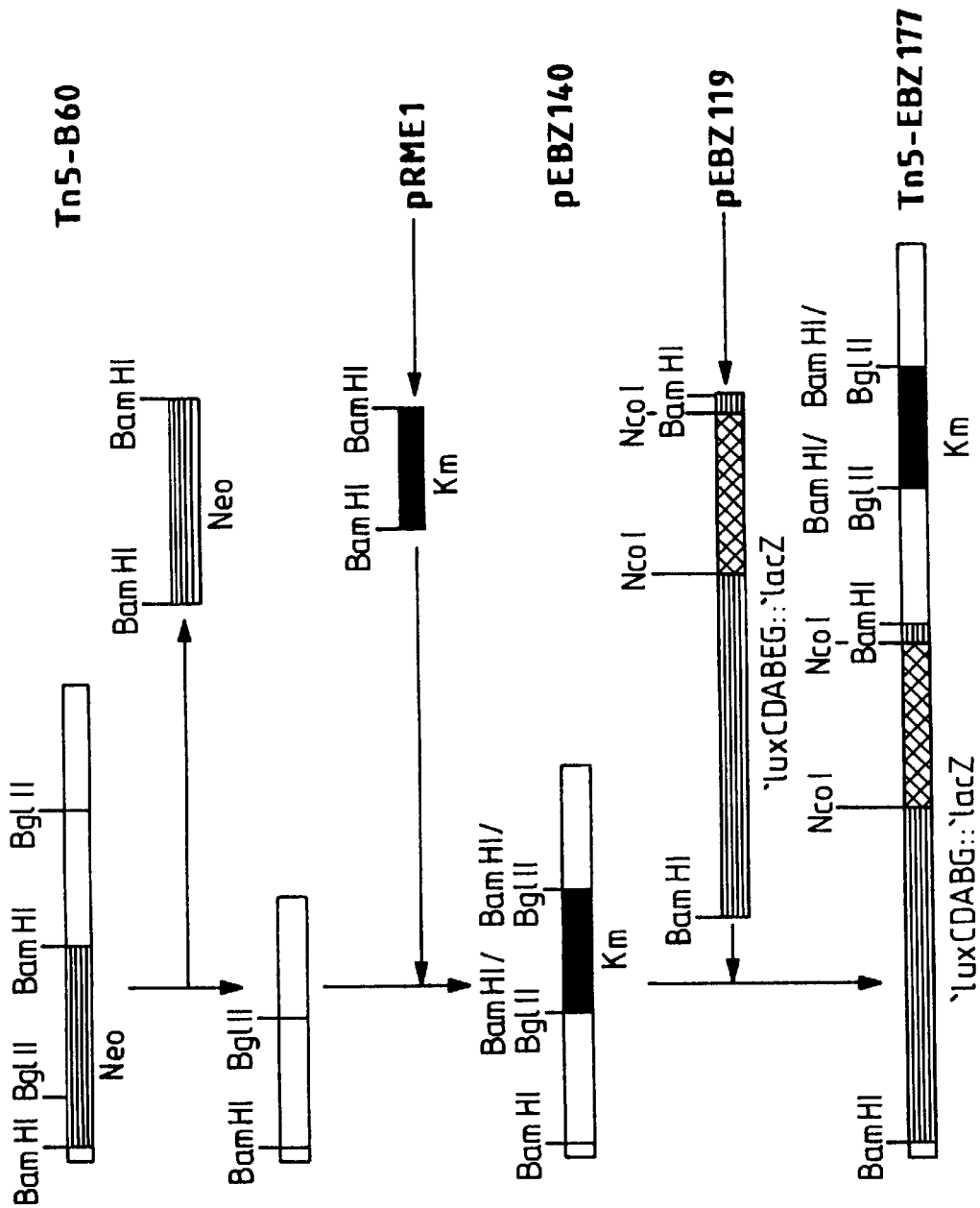

Fig. 2 Production of the transposable element Tn5-EBZ177 as a constituent of the plasmid pEBZ177

Production of the vector pEBZ112

Production of the recombinant plasmid pEBZ175

Effect of allylthiourea (ATU) on the luminescence of Photobacterium leiognathi

Effect of allylthiourea (ATU) on the luminescence of Vibrio harveyi

Effect of allylthiourea (ATU) on the luminescence of Nitrosomonas RST41-3/pEBZ154

Effect of allylthiourea (ATU) on the luminescence of Nitrosomonas RST41-3/pEBZ160

Effect of 2-chloro-6-(trichloromethyl)-pyridine (N-Serve) on the luminescence of Vibrio harveyi Effect of 2-chloro-6-(trichloromethyl)-pyridine (N-Serve) on the luminescence of Nitrosomonas RST41-3/pEBZ154

Effect of 2-chloro-6-(trichloromethyl)-pyridine (N-Serve) on the luminescence of Nitrosomonas RST41-3/pEBZ160

Effect of allylthiourea (ATU) on the luminescence of Nitrosomonas RST41-3/pEBZ154 in the presence of dodecanal Effect of allylthiourea (ATU) on the luminescence of Nitrosomonas RST41-3/pEBZ160 in the presence of dodecanal Effect of sewage with and without allylthiourea (ATU) on the luminescence of Nitrosomonas RST41-3/pEBZ175

Effect of sewage with and without allylthiourea on the luminescence of Nitrosomonas RST41-3/pEBZ175 in the presence of dodecanal Effect of 2-chloro-6-(trichloromethyl)-pyridine (N-Serve) on the luminescence of Nitrosomonas RST41-3/pEBZ145

LUMINESCENT NITRIFYING MICROORGANISMS

In the course of the aerobic or anaerobic decomposition of organic substances containing nitrogen, the nitrogen is released in the form of ammonium. The reaction of ammonium to form nitrate, or nitrification, is effected both in the soil and in water by nitrifying bacteria. The global nitrogen circuit is completed by this process: elementary nitrogen which is fixed due to microbial activity, and nitrogen fixed by microbial activity which is organically bound as a result of subsequent reactions, are converted by nitrification, after the above-mentioned release of ammonium, into products which are recycled as gaseous nitrogen compounds by what are termed denitrifying bacteria.

Nitrifying bacteria are gram-negative aerobic bacteria which are grouped together to form the Nitrobacteraceae family. Two groups of bacteria act together here: ammonium is first of all oxidised by ammonium oxidants in the presence of oxygen to form nitrite, which is subsequently reacted with oxygen to form to nitrate by nitrite oxidants. The oxidation of ammonium or nitrite constitutes the sole source of energy for the ammonium oxidants and nitrite oxidants, with the exception of some nitrite-oxidising strains of Nitrobacter. This method of obtaining energy is termed obligate chemolithotrophy. The carbon which is necessary for the synthesis of cell substance is introduced by the fixation of carbon dioxide. These bacteria are therefore autotrophic bacteria. Chemolithotrophic bacteria occupy a position of monopoly as regards their nitrification capacity. The rate of nitrification due to heterotrophic bacteria, i.e. those which increase using organic compounds as their source of carbon and energy, is lower by a factor of $10^3$ to $10^4$ than that of lithoautotrophic bacteria ("Allgemeine Mikrobiologie" ["*General Microbiology*"], H. G. Schlegel, Georg-Thieme Verlag, 1992). Due to their oxidation capacity as described above, lithotrophic bacteria are of great importance in the biological elimination of nitrogen in sewage treatment plants ("Der Einsatz von nitrifizierenden Bakterien zur biologischen Stickstoff-entfernung" ["*The use of nitrifying bacteria for the biological removal of nitrogen*"], E. Bock, M. Pohl, M. Bewernick, J. Lorenz, Korrespondenz Abwasser [*Sewage Correspondence*] January 1991, pages 34–39.

Known and Newly Developed Test Methods for the Measurement of Nitrification Inhibitors Nitrifying bacteria exhibit a sensitive behaviour in relation to various organic compounds ("Nitrification", J. I Prosser, IRS Press, Oxford-Washington DC, 1986), such as those which can also occur in sewage, for example. In particular, they have a pronounced sensitivity to compounds such as allylthiourea or 2-chloro-6-trichloromethylpyridine (nitrapyrine), very low concentrations of which (in the micromolar range) specifically inhibit nitrification ("British Library cataloguing in Publication Data: Nitrification Inhibition in the Treatment of Sewage", M. Richardson, Thames Water Authority, Nugent House, Reading, RG1 8DB, 1985; "Nitrification and Nitrogen Removal", B. Sharma and R. C. Ahlert in Water Research Vol. 13, Pergamon Press 1977, 897–925). The following methods, amongst others, have hitherto been described for measuring nitrification capacity: measurement of the ammonium consumption using an ammonium electrode consisting of immobilised nitrifying bacteria ("Ammonia electrode with immobilized nitrifying bacteria", M. Hikuma, T. Kubo, T. Yasuda, I. Karube, S. Suzuki, Anal. Chem. 1980, pages 1020–1024). Determination of the oxygen demand using an oxygen electrode. Determination of the nitrite or nitrate formed using colorimetric detection or by an HPLC technique with UV detection ("The impact of organic matter on nitric oxide formation by *Nitrosomonas europaea*", R. Stüven, M. Vollmer, E. Bock, Arch. Microbiol. 158, 1992, pages 439–443). Determination of the formation of nitric acid (nitrite) by measuring the pH. Moreover, the inhibition of nitrifying bacteria can be determined by cell count measurements or by means of specific gene sensors for bacteria which oxidise ammonia (EP 045 6047). In order to develop a method of measurement which constitutes an improvement compared with the methods available hitherto, which registers specific nitrification inhibitors within a very short time and with a high sensitivity, and which can easily be automated, we set ourselves the task of producing bioluminescent nitrifying bacteria.

Luminescent bacteria have been used for many years for testing chemical compounds for toxicity (see "Bioluminescence Assays", A. A. Bulich, CRC Press, Boca-Raton, Fla., USA, 1986, pages 57–74, for example). A test such as this is based on the fact that substances which are toxic to bacteria result in a decrease in bacterial luminescence. This is associated with the fact that cellular energy and reducing capacity in the form of reduced electron transfer agents are necessary for the said luminescence. Natural luminescent bacteria comprise a restricted group of bacteria which are predominantly found in seawater. Nitrifying bacteria which are naturally luminescent are unknown.

The underlying object of the present invention is to make use, for nitrification also, of the advantages which a toxicity measurement using luminescent test strains provides.

This aim had little prospect of success, for two reasons: (i) nitrifying bacteria are in an extremely unfavourable situation from an energetic point of view. Their substrates have a redox potential which is very strongly positive, so that their oxidation cannot be directly coupled with the reduction of NAD. However, reduced NAD is required for the reduction of carbon dioxide in the ribulose-bisphosphate cycle for the synthesis of cell substance. Moreover it is also involved in the bacterial luminescence reaction. There are experimental indications that the electrons produced during oxidation of the substrate are transferred into the respiratory sequence at the cytochrome c or a step, which results in a correspondingly low energy yield and cell yield. Part of this energy is used to return the electrons supplied in the cytochrome region via the respiratory sequence to the level of the pyridine nucleotides and to reduce the latter. The reverse transfer of electrons is therefore a vital mechanism for nitrifying bacteria. For the above-mentioned reasons, nitrifying bacteria increase extremely slowly, and generation times of at least seven hours are observed ("Nitrification—the bacterial oxidation of ammonia to nitrate", E. Bock, Forum Mikrobiologie [*Microbiology Forum*], January 1980). Both microbiological operations, and genetic operations in particular, using nitrifying bacteria are made more difficult for this reason. (ii) Nitrifying bacteria have hitherto hardly been investigated genetically. Nitrifying bacteria modified by genetic engineering have therefore not been described.

Production of Luminescent Nitrifying Bacteria

In order to achieve the aforementioned object, the genetic information for biological luminescence has been transferred according to the invention into obligate chemolithoautotrophic nitrifying microorganisms.

In particular, plasmid or transposon vectors have been produced in order to achieve this object, by means of which the genetic information for bacterial luminescence (lux-DNA) can be transferred into obligatorily chemolithoautotrophic nitrifying bacteria and a successful transfer event and ensuing expression of the lux genetic information can be identified in a simple manner, and the desired nitrifying bacteria which have been modified by means of genetic engineering can be selected. Vector systems consisting of an autonomously replicable broad host range plasmid or of a broad host range suicide plasmid or of a transposable element as a constituent of a broad host range suicide plasmid have been used for this purpose.

In one preferred embodiment, the vector system is pEBZ154, which is prepared by converting pEBZ110 to pEBZ119, pEBZ119 to pEBZ127, and pEB127 to pEB154. In another preferred embodiment, the vector system is pEBZ160, which is prepared by converting pEBZ110 to pEBZ119, pEBZ119 to pEBZ127, and pEBZ127 to pEBZ160. In still another preferred embodiment, the vector system is pEBZ175, which is prepared by converting pEBZ112 to pEBZ144, pEBZ144 to pEBZ173, and pEBZ173 to pEBZ175. In still another preferred embodiment, the vector system is pEBZ177, which is prepared by converting pEBZ140 to pEBZ177. In still another preferred embodiment, a vector is used that contains a lux-DNA or a lux-lacZ operon fusion as a reporter gene.

The present invention also relates to the use of the bioluminescent, nitrifying microorganisms obtainable by the aforementioned method for determining the viability of microorganisms during a nitrification process by measuring the decrease in luminescence. In this method of measurement the bioluminescent microorganisms are therefore used as an indicator for inhibitors which may possibly be present. In particular, inhibitors in a nitrifying biological sewage treatment plant can be detected in this manner.

EXAMPLES OF APPLICATION

The Production of Luminescent Nitrifying Bacteria

A pure culture of an ammonia-oxidising bacterium was isolated from sewage from Bayer AG in Leverkusen as an example to be used for the work. This bacterium was a Nitrosomonas-type with the designation RST41-3. This strain was assigned by microbiological and physiological investigations and by the use of a DNA gene sensor which is specific for Nitrosomonas (EP-0 456 047). Since it was questionable whether and under what conditions the capacity for bioluminescence would be transferred into the ammonia oxidants and would be manifested in the latter, the genetic information for luminescence (lux-DNA) was coupled with the genetic information for the disaccharidase β-galactosidase (lacZ-DNA) in a transcription fusion (operon fusion). Nitrosomonas RST41-3, as well as further separate isolates of ammonia-oxidising and nitrite-oxidising bacteria, naturally exhibited no β-galactosidase activity. It should thus be possible to identify a successful genetic transfer result and expression of the genetic information phenotypically by a blue coloration of the colonies on agar plates with 5-bromo-4-chloro-3-indolyl-β-D-galactopyranoside (X-Gal). This is particularly advantageous as a method for the extremely long incubation periods of several weeks of obligatorily chemolithoautotrophic bacteria such as nitrifying bacteria. Thus it was possible in addition to select not only according to the vector-determined resistance to antibiotics but also according to the attainment of β-galactosidase activity. It should thus be possible, in a simple manner, to identify the possible appearance of spontaneously resistant antibiotic-resistant mutants of the nitrifying bacteria which are to be genetically modified. Moreover, the nitrifying bacteria, which are presumably weakly luminescent due to their low energy content, can be identified in principle by the accumulation of blue dye.

The suicide broad host range vector pSUP202 ("A broad host range mobilization system for in vivo genetic engineering: transposon mutagenesis in gram-negative bacteria", R. Simon, U. Priefer, A. Pühler, Bio/Technology 1, 1983, pages 784–791) was used for the production of suicide plasmids (FIG. 1). In *Escherichia coli* this vector imparts resistance to ampicillin, chloramphenicol and tetracycline. According to an antibiogram of Nitrosomonas RST41-3 which was prepared, none of these resistances was present, particularly under the protracted, acidic incubation conditions for the selection process. The resistance to kanamycin, which had been proven to be beneficial, was therefore cloned in a first step. For this purpose the Tn903 resistance gene from the plasmid pRME1 (Dr. W. Messer, MPI für Molekular Genetik [*Max Planck Institute for Molecular Genetics*], Berlin), which had proved to be easy to manipulate in previous work ("Regulation of hydrogenase gene expression and formation of catalytically active hydrogenase in *Alcaligenes eutrophus*", G. Eberz, dissertation for the award of a doctorate of the Free University of Berlin, 1989), was cloned into the chloramphenicol resistance gene of pSUP202. The derivative produced was called pSUP202-1.

In a further step the luciferase gene sequence, which was without a promoter but which carried a ribosome binding site, of the right-hand luciferase operon from *Vibrio fisherii*, which consists of luxCDABEG genes ("Molecular Biology of Bacterial Luminescence", E. A. Meighen, Microbiological Reviews 55, 1991, pages 123–142; "Physiological, Biochemical and Genetic Control of Bacterial Bioluminescence", E. A. Meighen and P. V. Dunlap, in: Advances in Microbial Physiology 34, 1993, 1–67), was cloned as a Bam HI fragment into the *E. coli* expression vector pUC18 with an orientation such that the genetic information for luminescence was inserted into corresponding transformants. The hybrid plasmid produced was given the designation pEBZ110. The luciferase DNA originated from transposon Tn4431 ("Transposon Tn4431 Mutagenesis of *Xanthomonas campestris* pv. *campestris:* Characterization of a Nonpathogenic Mutant and Cloning of a Locus for Pathogenicity", J. J. Shaw, L. G. Settles, C. I. Kado, Molecular Plant-Microbe Interactions, 1, 1985, pages 39–45). The lux-DNA used contained an Nco I cleavage site which was situated in the luxG gene, which itself is not necessary for the manifestation of luminescence. The vector pUC18 contains no such recognition sequence. In order to fuse the luciferase information with the genetic information for β-galactosidase, it was possible to use a 'lacZ cassette, which was without a promoter but which was provided with a ribosome binding site, for insertion into the Nco I cleavage site of pEBZ110, as has been described for the plasmid pSUP301-'lacZ ("A New Family of RSF1010-derived expression and lac-fusion broad host range vectors for gram-negative Bacteria", M. Labes, A. Pühler, R. Simon, Gene 89, pages 37–46, 1990). A 'lacZ cassette, which was provided on both sides with a more extensive polylinker consisting of possible recognition sites for restriction endonuclease, was used for the present work. An NcoI cleavage site situated inside the polylinker could be used to clone the 'lacZ cassette into the NcoI cleavage site of pEBZ110 described above. The hybrid plasmid produced was designated pEBZ119. In *E. coli* bacteria with a deletion in the lacZ gene in the presence of IPTG it imparts both luminescence and β-galactosidase activity to the inducer of the promoter of the pUC18 expression vector used.

The 'lux-'lacZ transcription fusion was cut as a Bam HI fragment from pEBZ119 and inserted into the Bam HI cleavage site of the tetracycline resistance gene of pSUP202-1 so that the tetracycline resistance gene promoter initiated the expression of the operon fusion. The plasmid pEBZ127 produced in this manner brought about both luminescence and β-galactosidase activity in E. coli.

Different Pst I fragments isolated from the entire DNA of Nitrosomonas RST41-3 were incorporated in the Pst I cleavage site of the ampicillin resistance gene of pEBZ127. Two of the clones obtained in this manner were given the designations pEBZ154 (containing a Nitrosomonas DNA fragment of size about 2.7 kb) and pEBZ160 (containing a Nitrosomonas DNA fragment of size about 10 to 11 kb). This step is necessary because the base replicon of these plasmids can be propagated in E. coli and transferred into different gram-negative bacteria but is not replicable in the latter. However, the transferred hybrid plasmids should be incorporated into the genome of ammonia oxidants by a cellular DNA recombination mechanism of the bacterial host with the inclusion of the cloned, homologous host DNA.

The construction of the transposable element (FIG. 2) started from the Tn5 derivative B60 ("New derivatives of transposon Tn5 suitable for mobilization of replicons, generation of operon fusions and induction of genes in gram-negative bacteria", R. Simon, J. Quandt, W. Klipp, Gene 80, 1989, pages 161–169). For this purpose the neomycin resistance gene, including an outwardly oriented tac promoter, both of which are situated on a Bam HI fragment of the transposon fraction of pSUP-Tn5-B60, were first of all deleted. The kanamycin resistance gene from pRMEI (see above) was cloned as a Bam HI fragment into the Bgl II cleavage site of the transposon modified in this manner; it can no longer be cut by Bam HI restriction from the construction produced (pEBZ140). The 'lux-'lacZ fusion from pEBZ119 was inserted into the single Bam HI recognition sequence obtained by the above deletion so that the transcription could be initiated starting from the left end of the transposon. The transposon plasmid pEBZ117 produced in this manner accordingly consisted of a 'lux-'lacZ promoter-locating transposon which is situated in a suicide broad host range vector.

Figure 3:
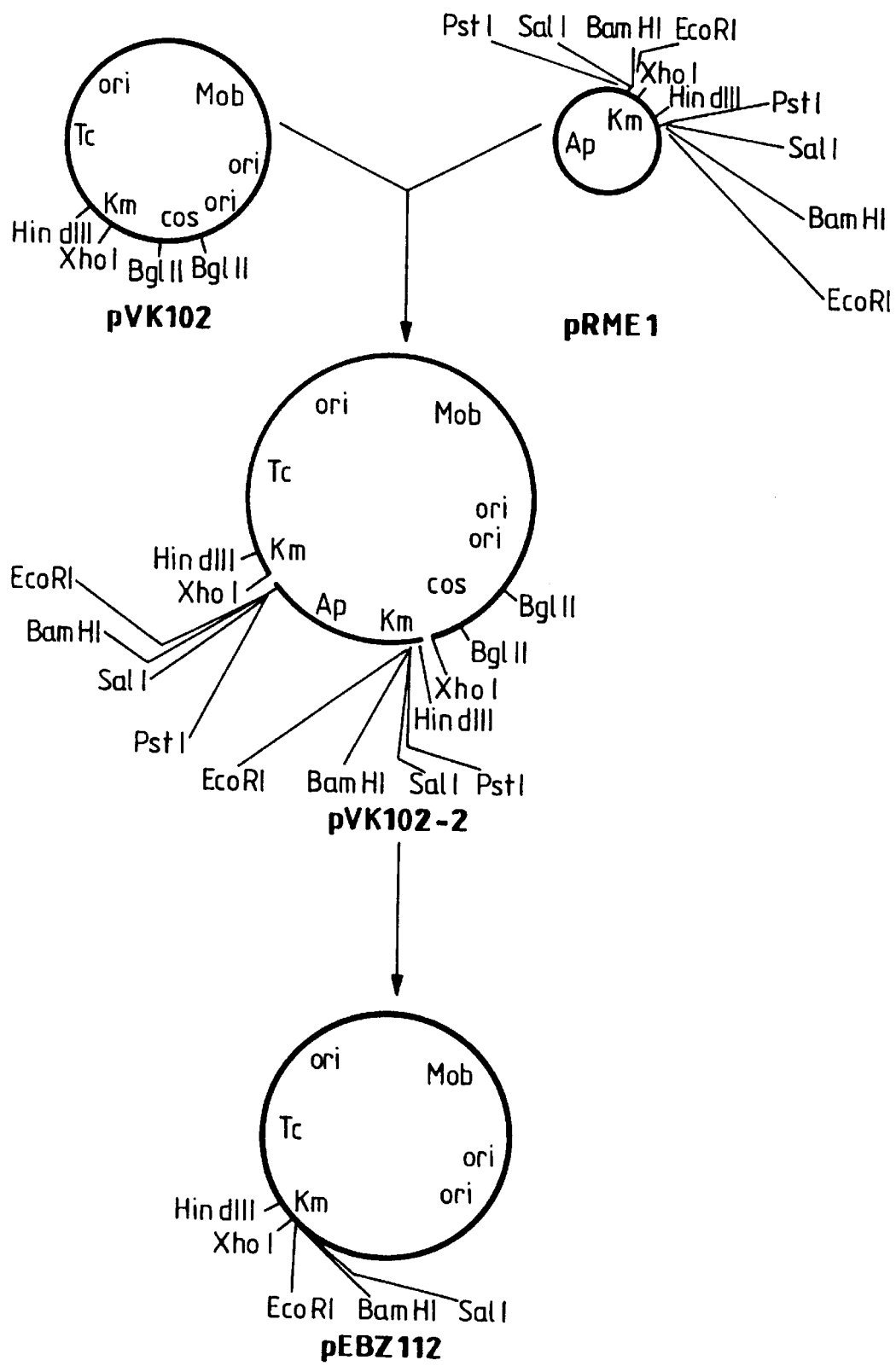
Figure 4:
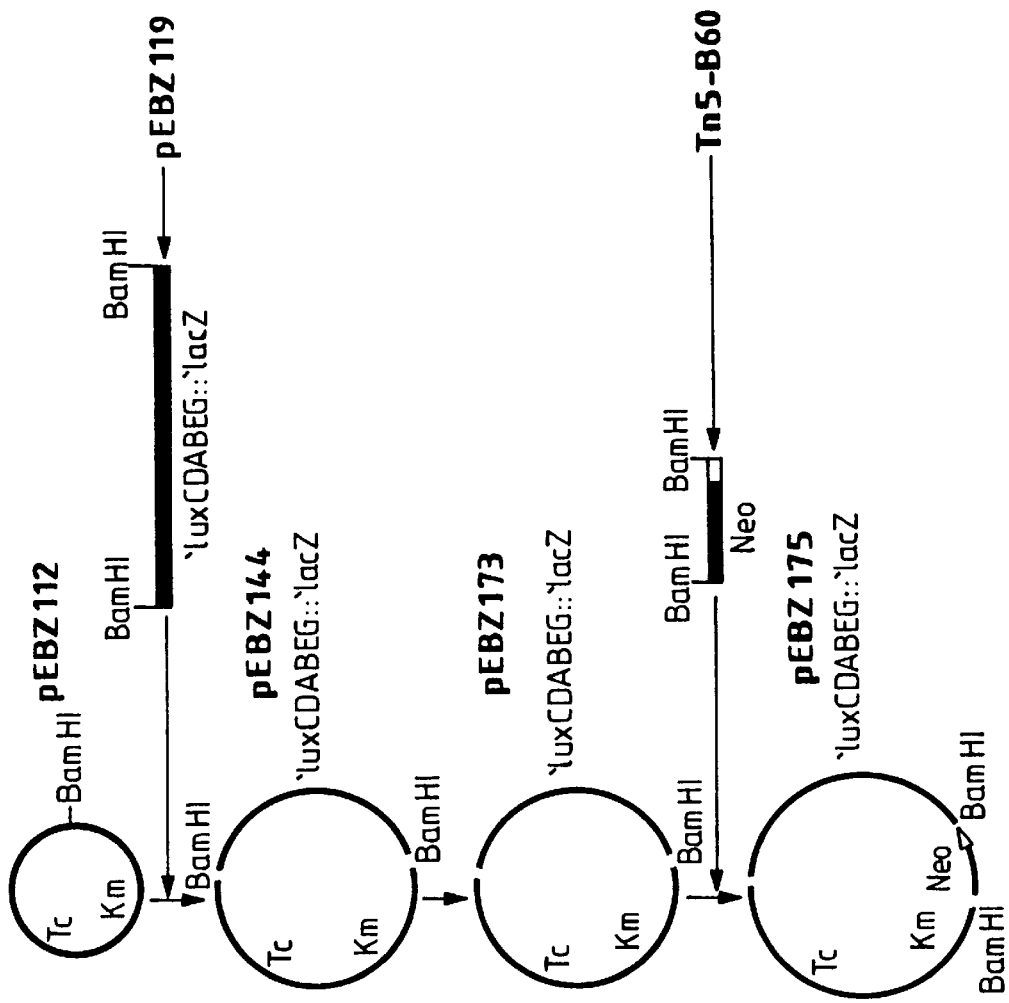

The production of the 'lux-'lacZ vector, which is replicable in various gram-negative bacteria, was carried out as follows (FIGS. 3 and 4): in a first step the cosmid vector pVK102 ("Wide host range cloning vectors: a cosmid clone bank of an Agrobacterium Ti plasmid", V. C. Knauf, E. W. Nester, Plasmid 8, 1982, pages 45–54) was linearised with XhoI and ligated with the plasmid pRME1 cleaved with the XhoI (FIG. 3). The plasmid pRME1 consists of pBR322 which contains a kanamycin resistance gene cassette, which is bounded on both sides by a polylinker, at the HindIII cleavage site of the tetracycline resistance gene. This polylinker contains several recognition sites for restriction endonucleases, such as Eco RI, Bam HI, Sal I or Pst I, for example (FIG. 3). One of the contained ligation products (pVK102-2) was doubly cleaved with Bgl II and Pst I, and the largest digestion product obtained was isolated and religated after pretreatment with Klenow polymerase. In this manner the predominant pRME1 fraction and the cos site were eliminated from the cointegrate, whereby the vector thus produced (pEBZ112) carried a small multiple cloning site (mcs) directly adjacent to the kanamycin resistance gene. Due to this procedure, the kanamycin resistance gene in pEBZ112 was composed both of parts of the kanamycin resistance gene from pVK102 and of parts of the kanamycin resistance gene cassette from pRME1. Amongst other sites, this mcs contained a single Bam HI cleavage site (FIG. 4) into which the 'lux-'lacZ fusion could then be inserted as a Bam HI fragment (pEBZ144). This vector was incompletely cleaved with Bam HI, filled with Klenow polymerase and religated in order to destroy the Bam HI cleavage site situated at the end of the 'lux-'lacZ operon. The vector pEBZ173 which was produced by this method only carries one Bam HI recognition sequence, which is situated in the mcs in front of the 'lux-'lacZ operon. The Bam HI fragment from the suicide transposon plasmid pSUP-Tn5-B60 (see above), which carried the neomycin resistance gene and the outwardly directed tac promoter, was cloned into this singular Bam HI cleavage site in such a way that the tac promoter initiated the transcription of the 'lux-'lacZ fusion. The last-mentioned plasmid (pEBZ175) imparted the capacity for luminescence and β-galactosidase activity, which can be induced with IPTG, to corresponding lacI$^q$ E. coli bacteria.

In a batch which was processed in parallel, the entire lux regulon from V. fischeri, consisting of the regulation genes luxR and I and of the above-mentioned lux structural genes, was cloned as a Sal I fragment into the vector pVK102. The lux DNA originated from the recombinant plasmid pJE202 ("Identification of genes and gene products necessary for bacterial bioluminescence", J. Engebrecht and M. Silverman, Proc. Natl. Acad. Sci. USA, 1984, pages 4154–4158). The plasmid produced was given the designation pEBZ145.

Genetic Transfer of the 'lux-'lacZ Fusion Constructions into Nitrosomonas sp. RST41-3

Because they are situated in vectors with a broad capacity for mobility into various gram-negative bacteria, the luciferase-encoding plasmids produced could be mobilised towards Nitrosomonas RST41-3 in a two-parent crossing with the Escherichia coli strain S17-1 as the donor ("A broad host range mobilization system for in vivo genetic engineering: transposon mutagenesis in gram-negative bacteria", R. Simon, U. Priefer, A. Pühler, Bio/Technology 1, 1983, pages 784–791). In this respect the following conjugation conditions were selected: incubation of 80 µl of a well-grown and washed culture of the Nitrosomonas recipient, adjusted to about $10^{10}$ cells per ml, together with 80 µl of the E. coli donor adjusted to $10^6$ cells per ml, for two days at 28° C. on a solid minimal medium was chosen as the non-selective step. In this connection it was possible to use a medium such as that cited in the publication "Classification of eight new species of ammonia-oxidizing bacteria: *Nitrosomonas communis* sp. nov., *Nitrosomonas ureae* sp. nov., *Nitrosomonas aestuarii* sp. nov., *Nitrosomonas marina* sp. nov., *Nitrosomonas nitrosa* sp. nov., *Nitrosomonas eutropha* sp. nov., *Nitrosomonas oligotropha* sp. nov. and *Nitrosomonas halophila* sp. nov." (H.-P. Koops, B. Böttcher, U. C. Möller, A. Pommerening-Röser, G. Stehr, Journal of General Microbiology 137, 1991, pages 1689–1699). In addition, the carbon source necessary for the E. coli donor was added to the medium in the form of 0.05% glucose as well as proline and thiamine. The parents were elutriated with minimal medium without glucose, proline and thiamine and suitable dilution series were transferred using a spatula on to selective plates. The selective plates consisted of the above-mentioned minimal medium without glucose, proline and thiamine, but with nalidixic acid at a concentration of 50 µg/ml and kanamycin at a concentration of 15 µg/ml as well as X-Gal. The Nitrosomonas strain used exhibited a pronounced resistance to nalidixic acid. Only plasmid-carrying descendants of this strain also have the plasmid-encoded resistance to kanamycin. After about two months, Nitrosomonas transconjugates appeared. The successful transcription of the 'lux sequence, and the expression of β-galactosidase in the Nitrosomonas hosts after transfer of the lux-lacZ fusion, could be seen after about two months by a blue coloration of the small Nitrosomonas colonies, which resulted in an acidification of the medium in the usual manner (colour change of the phenol red pH indicator, 10 mg/l).

All the transconjugate colonies were coloured blue on indicator plates after transfer of the suicide plasmids pEBZ154 and pEBZ160 and after transfer of the plasmid pEBZ175. In contrast, only a few transconjugate colonies which were coloured blue appeared amongst the isolated colonies after transfer of the plasmid pEBZ177. This indicates that the transposon present in pEBZ177 first had to transpose into the Nitrosomonas genome so that the genetic information for β-galactosidase could be read. In this respect, the transposition had to be effected so that a separate Nitrosomonas promoter served to incorporate the lacZ information.

The appearance of these transconjugates which exhibited β-galactosidase firstly verifies that the E. coli consensus tac promoter, as well as the promoter of the tetracycline-resistant gene from pEBZ154 and pEBZ160, which originates from pMB9 ("Gene und Klone" ["Genes and Clones"] E.-L. Winnacker, Verlag Chemie, 1984, pages 115–119) is capable of functioning in an obligate chemolithoautotrophic bacterium such as Nitrosomonas. The fact that descendants exhibiting β-galactosidase also appeared in addition to kanamycin-resistant descendants after transfer of the 'lux-'lacZ-Tn5 derivative into Nitrosomonas, firstly demonstrates that the Tn5 derivative which was produced transposed in the obligate chemolithotrope.

After transfer of the lux plasmid pEBZ145, the transconjugates merely had to be -identified as recombinant clones on the selective medium by means of their kanamycin-resistant phenotype.

Inhibition Measurements with Luminescent Nitrifying Bacteria

The blue transconjugates produced and the Nitrosomonas RST41-3/pEPZ145 transconjugates were purified on selective medium, inoculated into 20 ml of liquid selective medium without X-Gal and cultivated for several days at 28° C. After visible growth had occurred, 200 ml of the same medium were inoculated with this preliminary culture and incubated in a corresponding manner.

Figure 5:
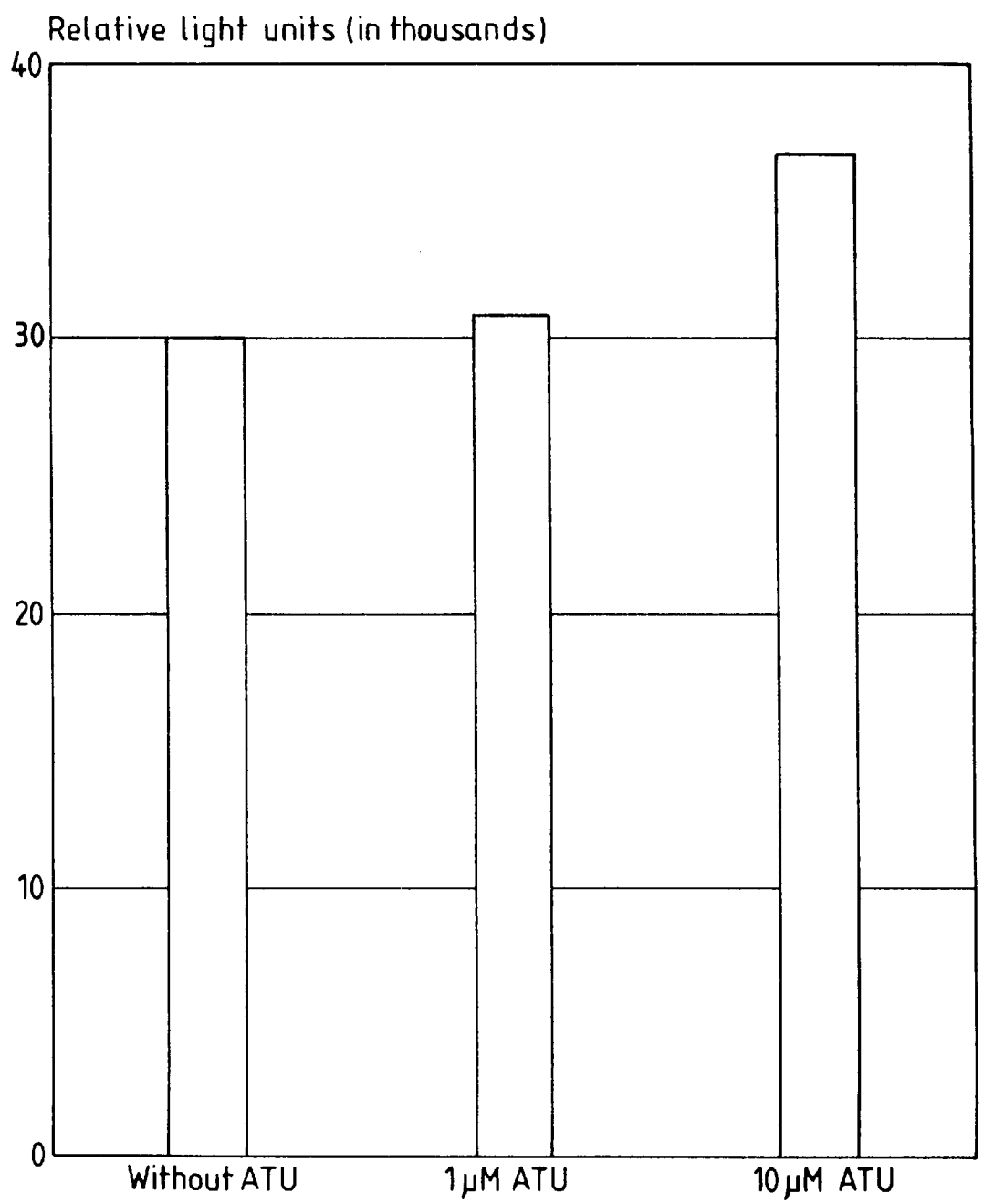
Figure 6:
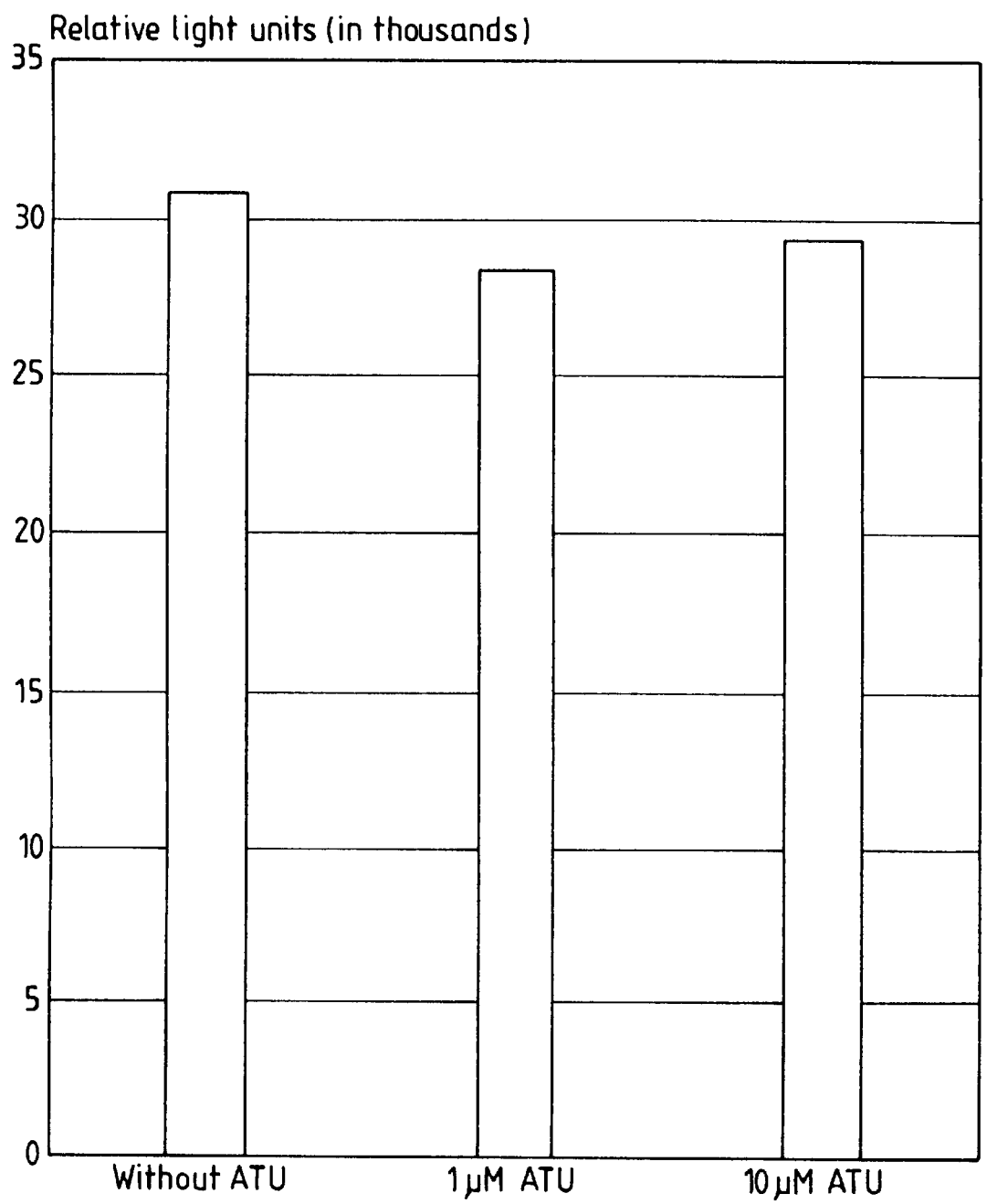
Figure 7:
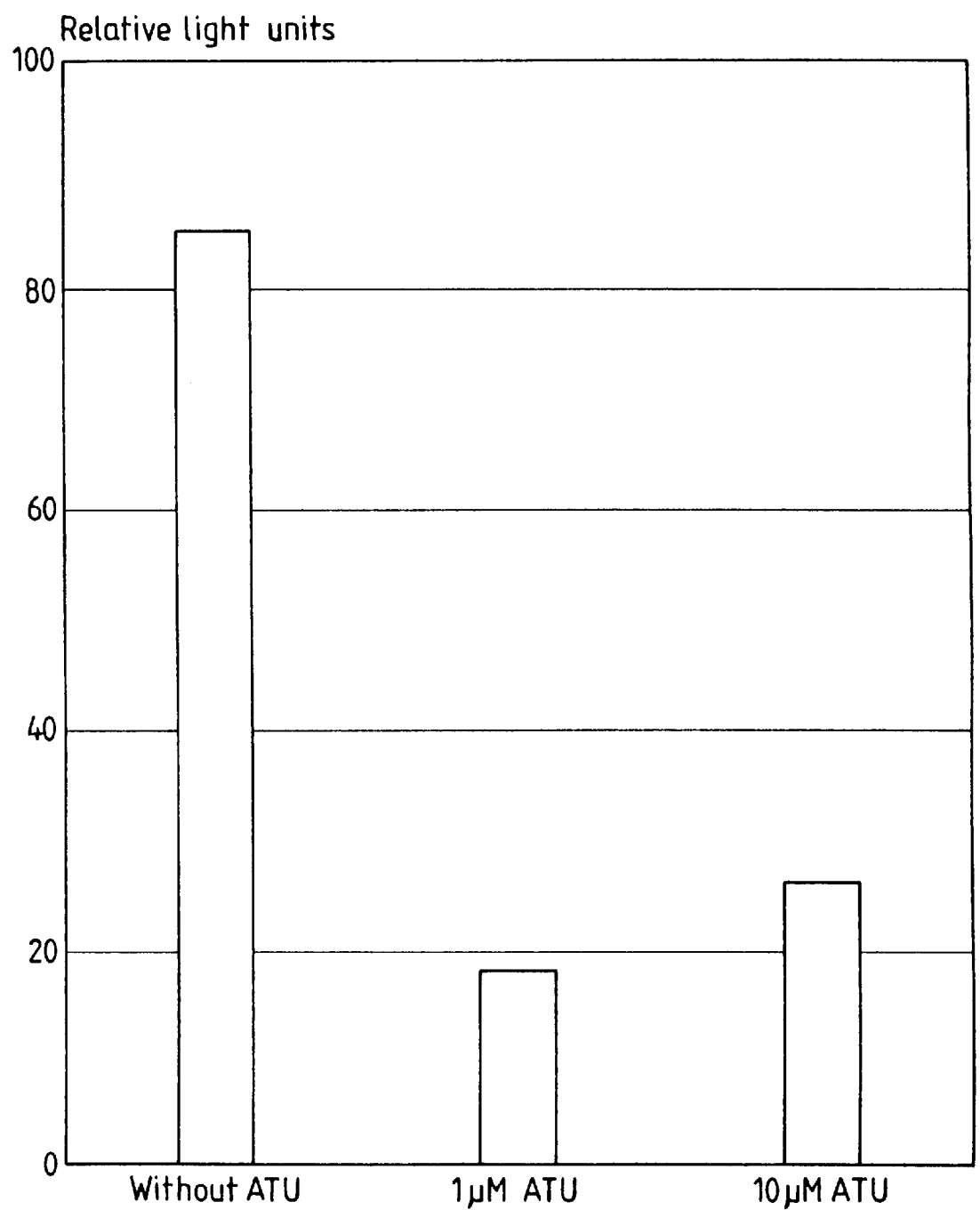
Figure 8:
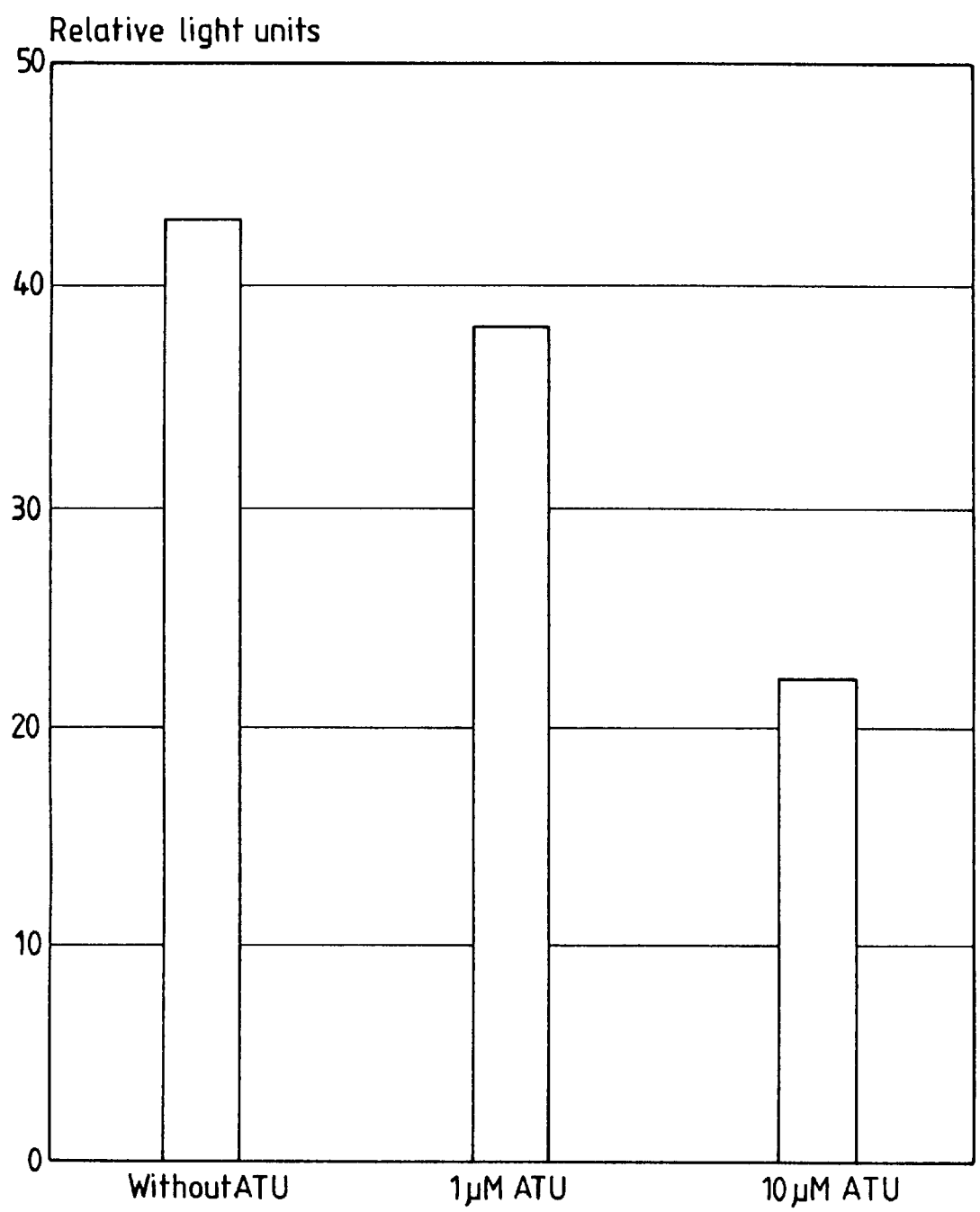

All the Nitrosomonas derivatives produced exhibited autonomous luminescence. For the luminescence measurements, the isolates were harvested in the stationary growth phase, concentrated about two hundred times in fresh minimal medium without nalidixic acid and kanamycin, and 0.1 to 0.2 ml were used for 60 seconds for the luminescence measurement (Lumac/3M Biocounter M2010A tube luminometer; RLU blank value: 10–12). This was significantly lower by comparison with the natural luminescent bacteria Photobacterium leiognathi (ATCC 33469) and Vibrio harveyi (ATCC14126) after cultivation in 246 medium (medium according to the "Catalogue of Strains 1993", Deutsche Sammlung von Mikroorganismen und Zellkulturen GmbH, Braunschweig [German Collection of Microorganisms and Cell Cultures Ltd., Brunswick]) and measurement for 60 seconds (FIGS. 5 and 6). In contrast to the latter, however, their luminescence could be significantly reduced by dosing with low concentrations of the nitrification inhibitor allylthiourea, as illustrated for the strains N. RST41-3/pEBZ154 and N. RST41-3/pEBZ160, for example (FIGS. 7 and 8).

Figure 9:
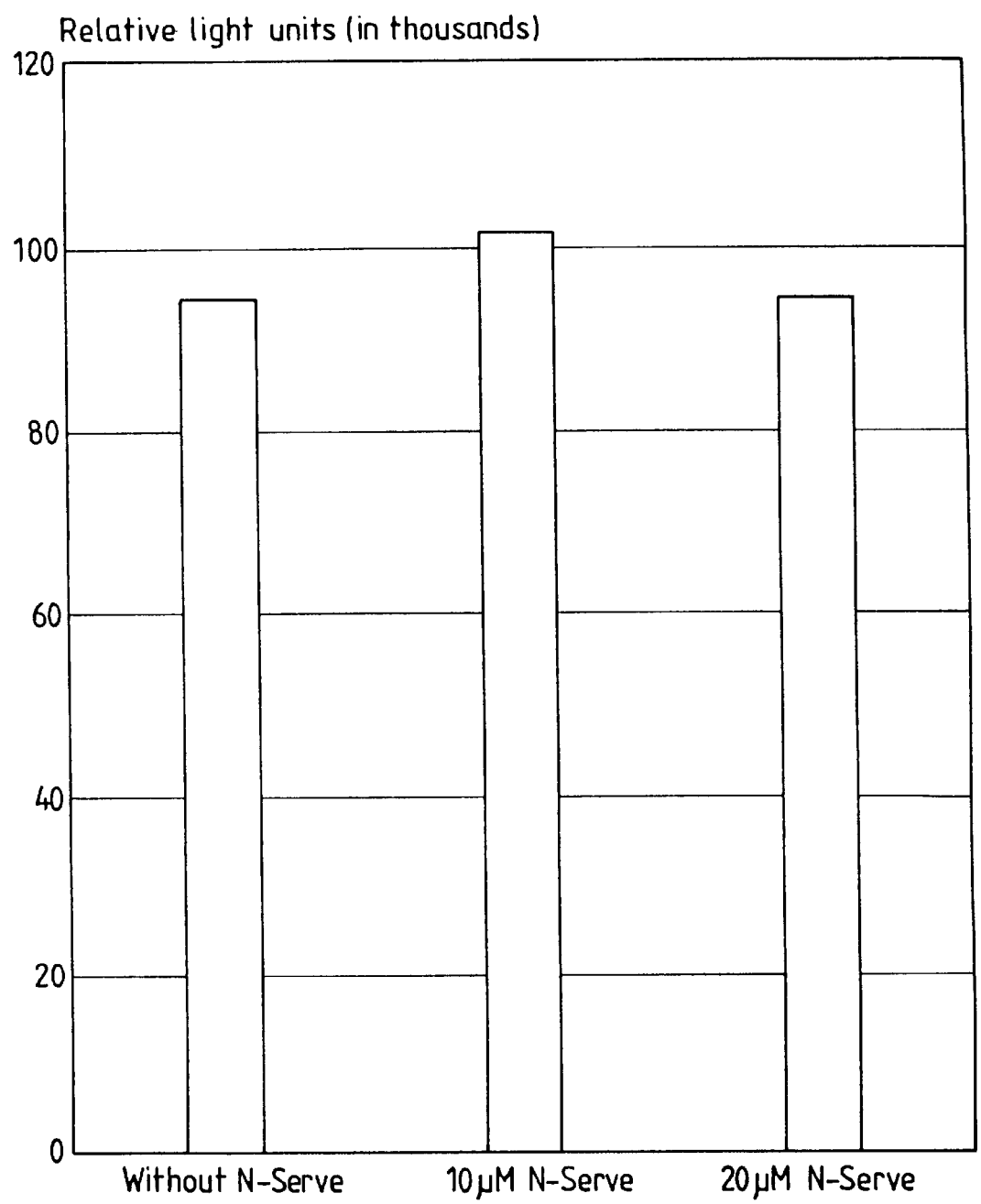
Figure 10:
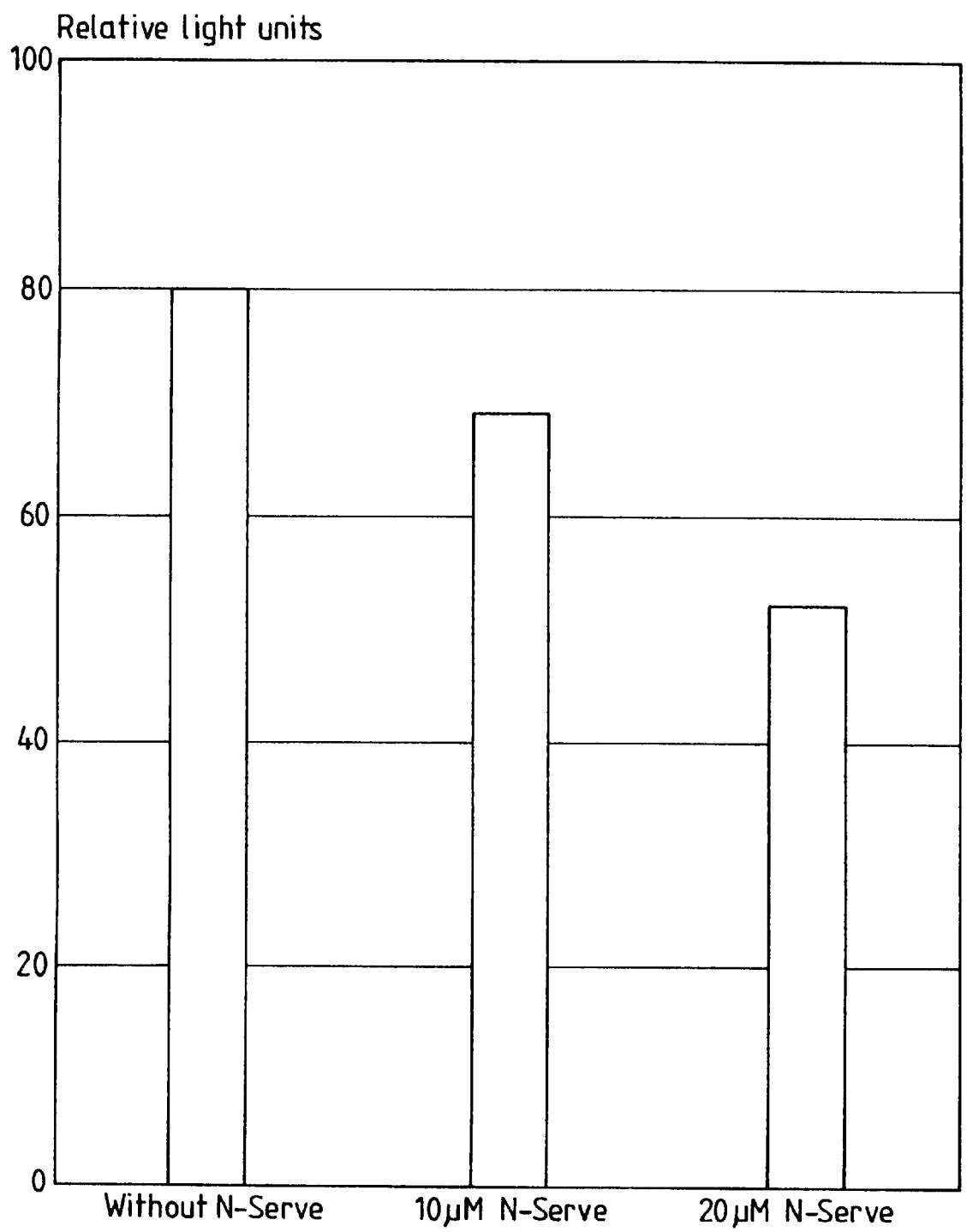
Figure 11:
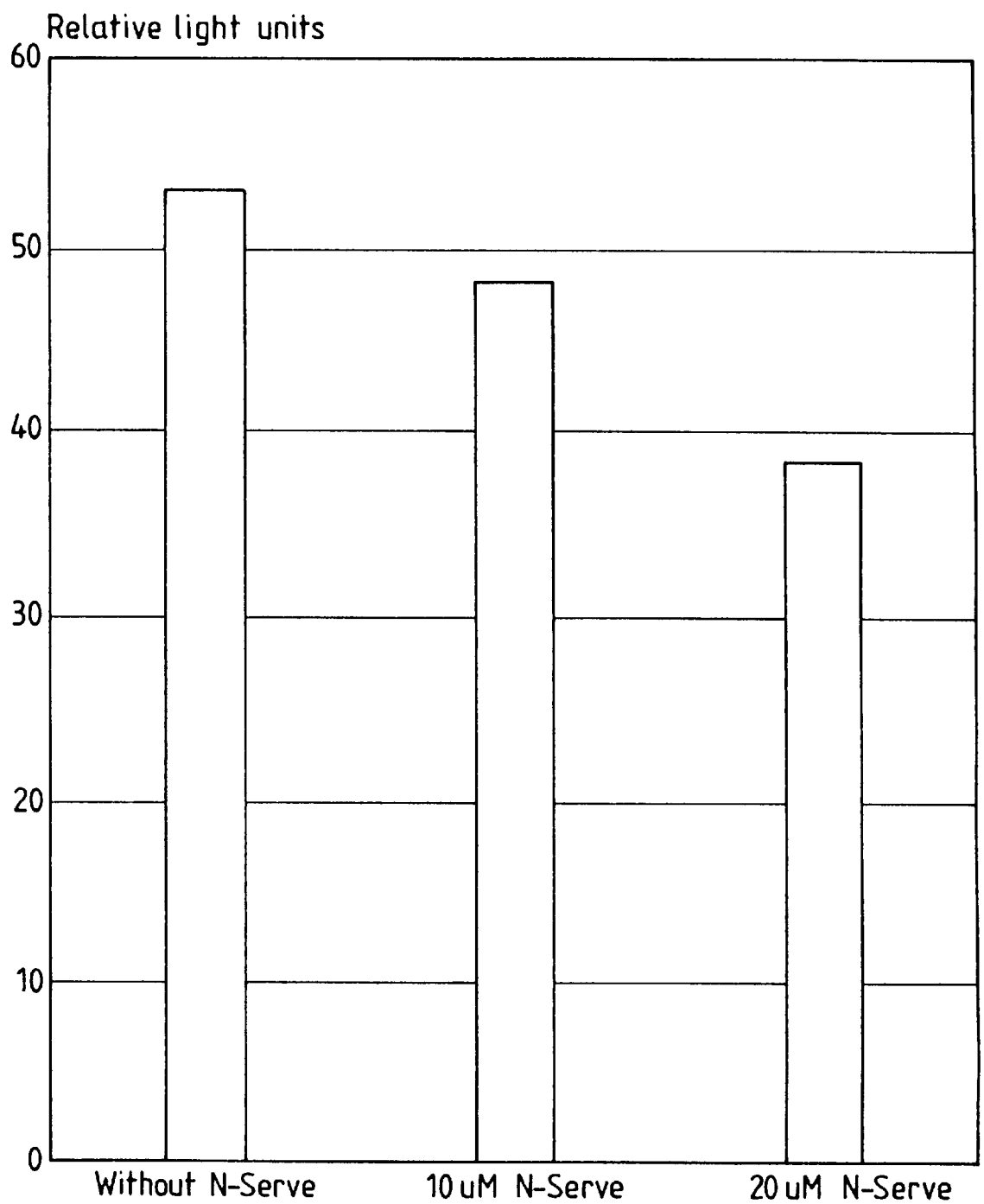

Moreover, small doses of the nitrification inhibitor N-Serve (2-chloro-6-(trichloromethyl)-pyridine) only resulted in a significant decrease of luminous intensity when added to the luminescent ammonia oxidants N. RST41-3/pEBZ154 and N. RST41-3/pEBZ160 (FIGS. 9, 10 and 11).

Figure 12:
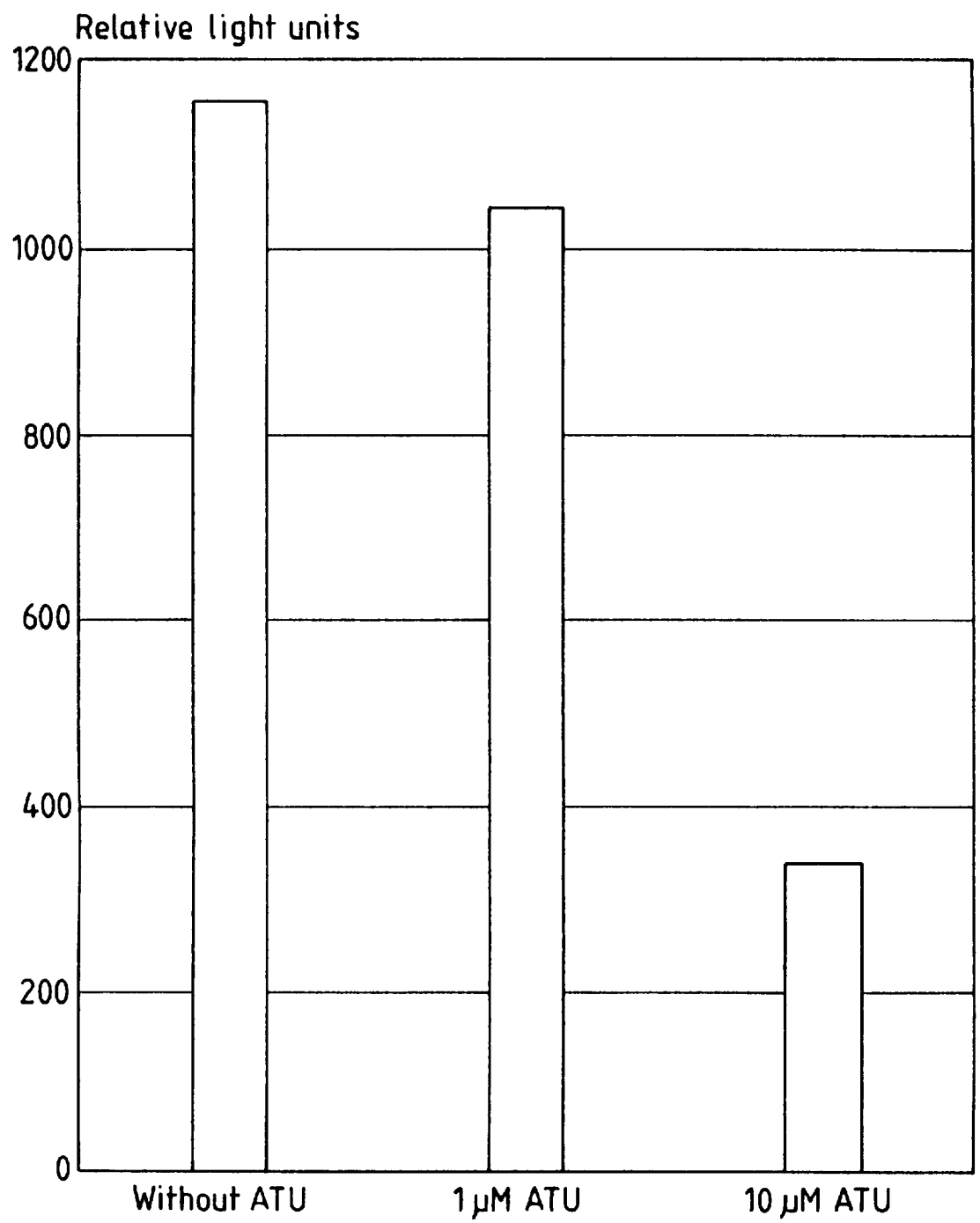
Figure 13:
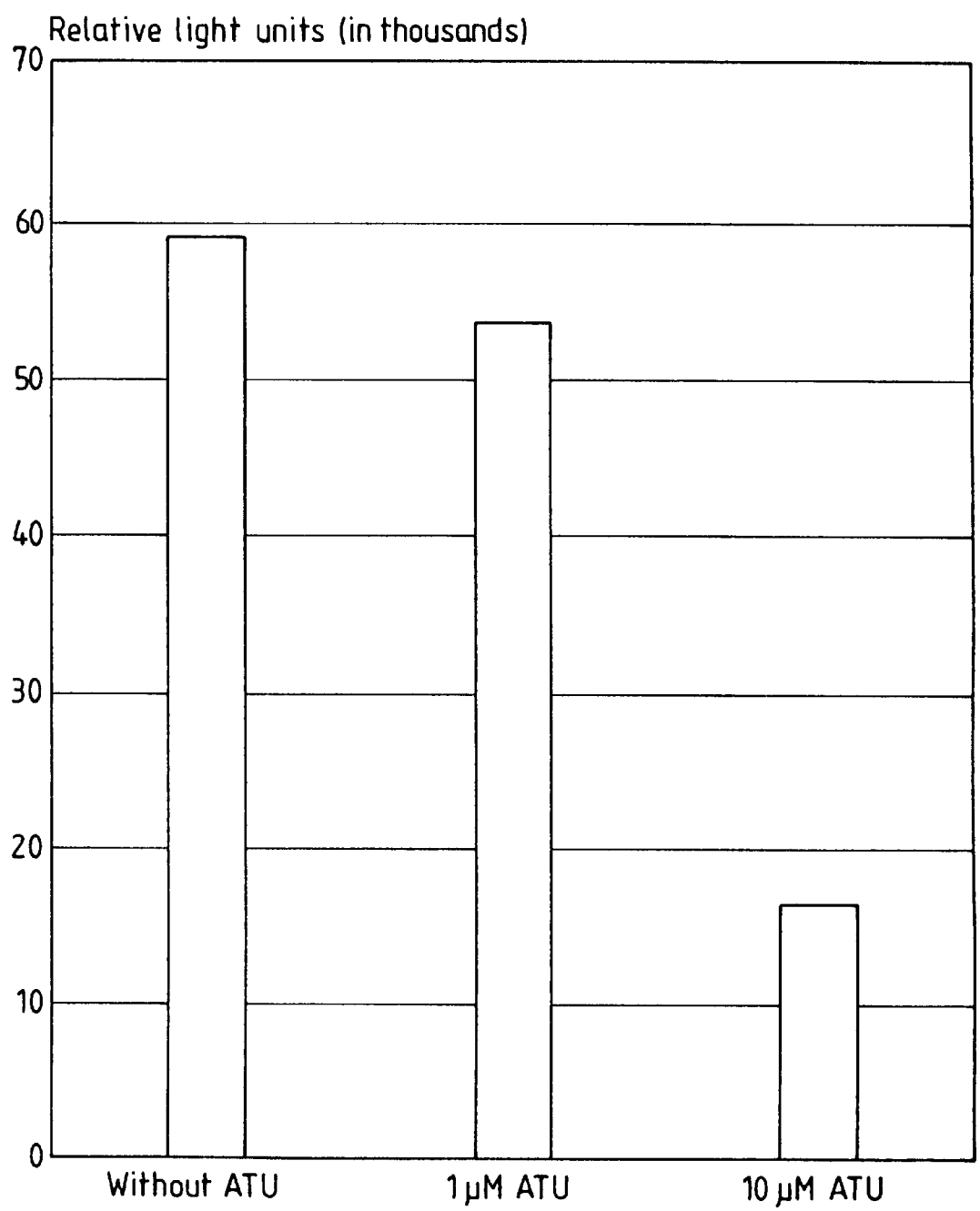

Since it is known that the luminescence of natural luminescent bacteria can be increased by the addition of the luminescence substrate, a long chain aldehyde, dodecanal ("Bacterial Bioluminescence: Isolation and Expression of the Luciferase Genes from Vibrio harveyi", R. Belas, A. Mileham, D. Cohn, M. Hilmen, M. Simon, M. Silverman, Science 218, pages 791–793, 1982) was added to the test batch immediately before the luminescence measurement. The ammonia oxidants which had been modified by mesas of genetic engineering also reacted with a strong increase in luminescence. This was drastically reduced in the presence of the nitrification inhibitor allylthiourea, however (FIGS. 12 and 13).

Figure 14:
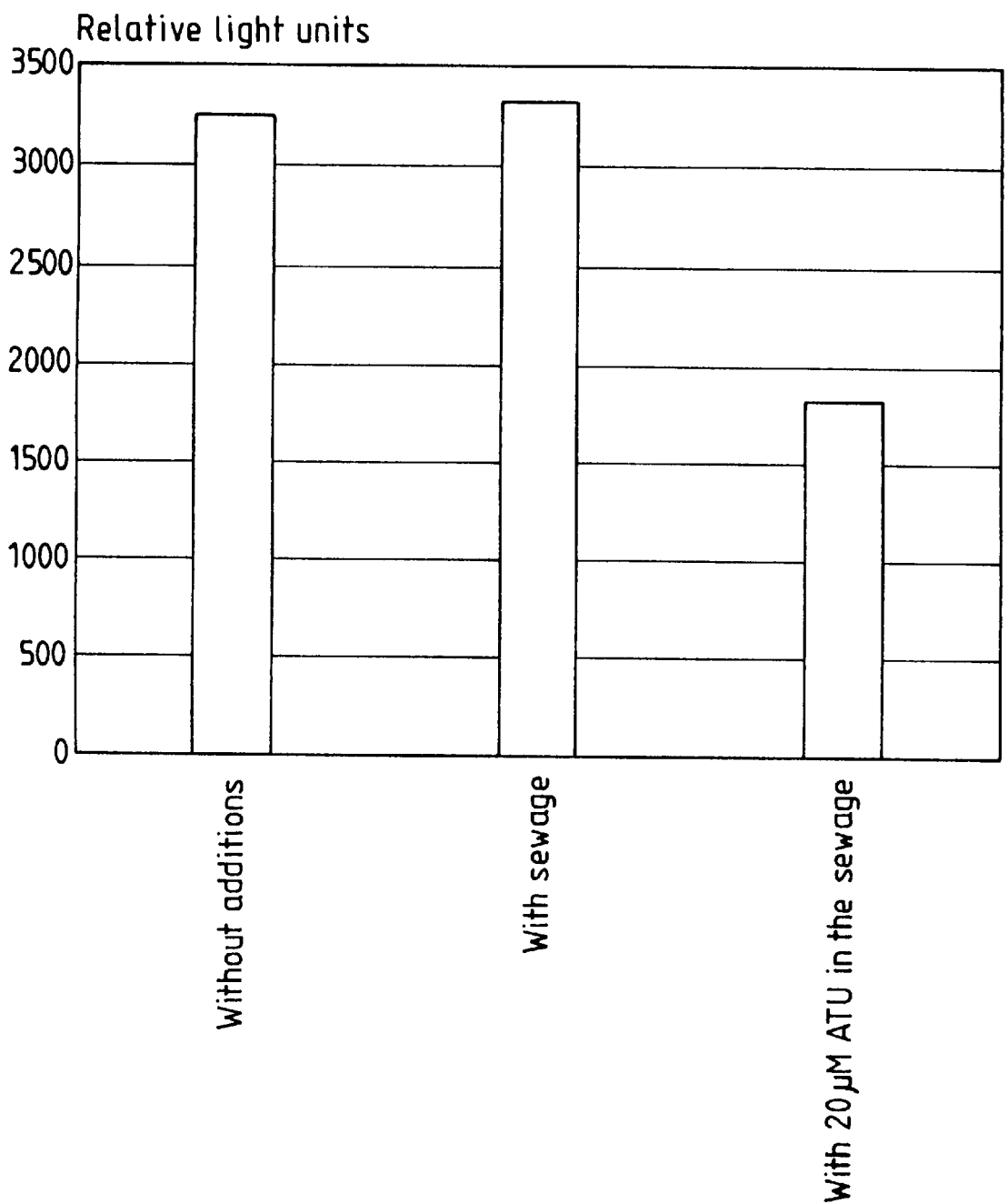
Figure 15:
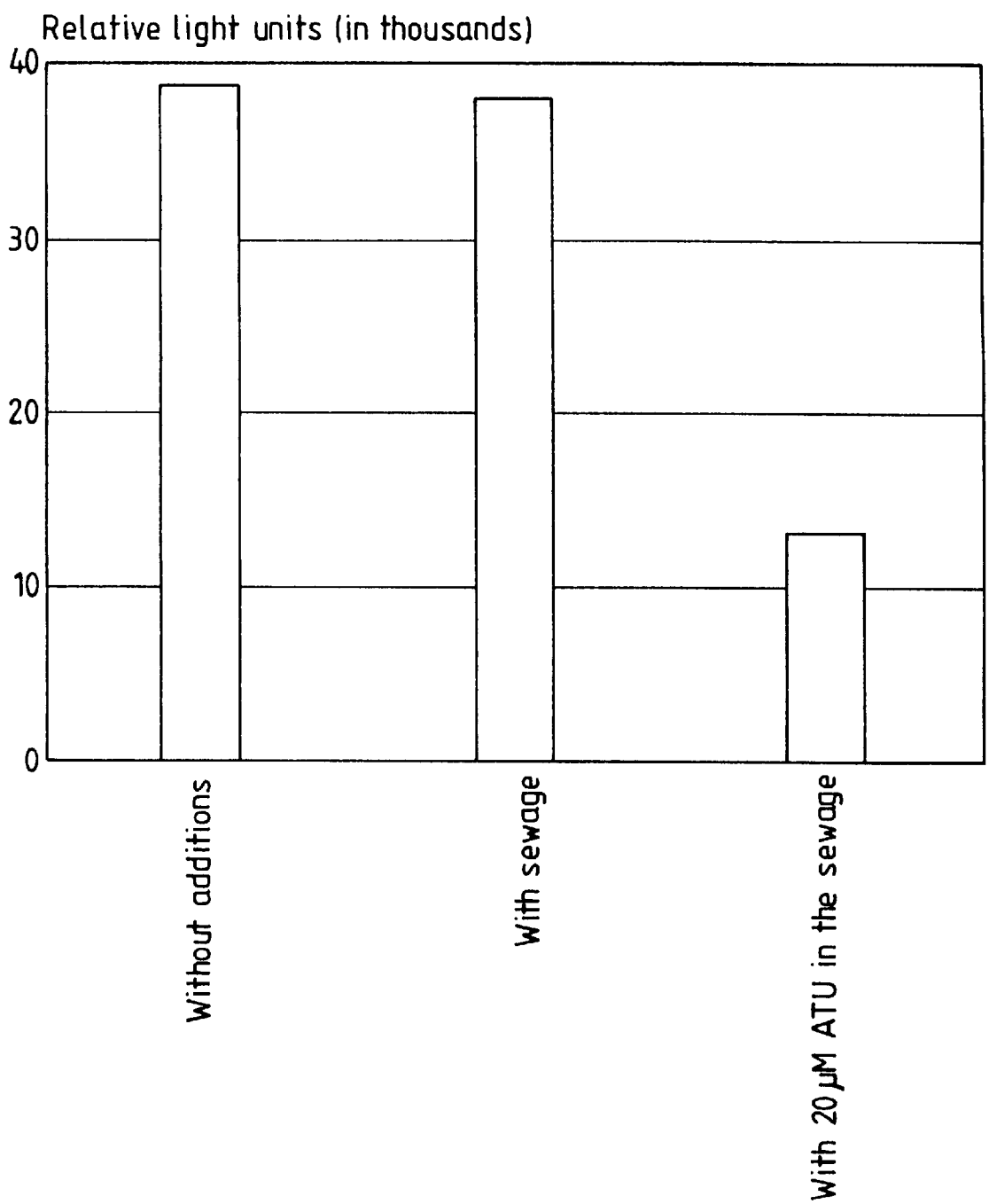

The strains Nitrosomonas RST41-3/pEBZ160 and N. RST41-3/pEBZ175 were thereupon tested for their capacity to indicate the presence of allylthiourea in the discharge from the sewage treatment plant of Bayer AG in Leverkusen. For these tests the sewage was mixed with one volume of double-concentrated medium. One part of this mixture was added to two parts of the bacterial suspension. In fact, both strains reacted with a drastic decrease in luminescence only in the presence of added allylthiourea. The clone Ns. RST41-3/pEBZ175 which was used had a comparatively high autonomous luminescence (FIG. 14). The luminescence of this construction could also be increased by dodecanal, wherein 20 μM of allylthiourea in the sewage sample used likewise resulted in a decrease in luminescence (FIG. 15).

Figure 16:
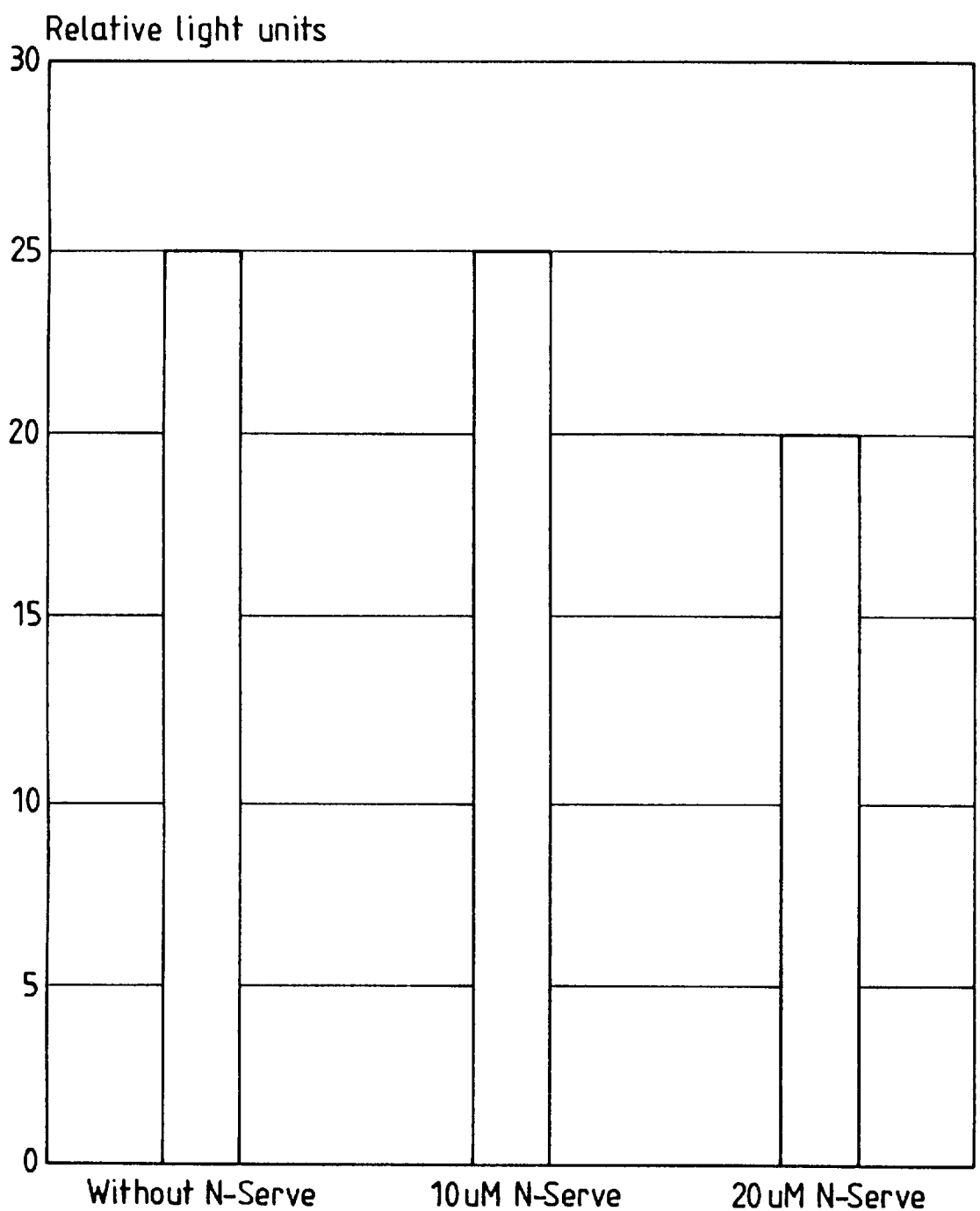

The strain Ns. RST41-3/pEBZ145 only exhibited extremely weak luminescence, which could be reduced in the presence of 20 μM of N-Serve, however (FIG. 16).

Advantage of the Newly Developed Test Method for Detecting Nitrification Inhibitors Luminescent nitrifying bacteria open up the possibility of identifying nitrification inhibitors selectively and sensitively using a method which can easily be automated. Toxic bursts of a nitrification inhibitor in sewage can be registered rapidly, which results in a correspondingly long period of time for the implementation of measures for the protection of a sewage treatment plant. In addition, the nitrifying bacteria produced enable the preliminary step of biological nitrogen elimination in sewage treatment plants or in other complex matrices to be investigated and optimised by way of a simple measurement of the luminescence. This is possible inasmuch as the bioluminescence reflects the vitality of the microorganism cell. Other biotechnological processes in which chemolithotrophic bacteria participate can be optimised in an analogous manner using the same procedure. A leaching process can be considered in this respect, for example.

A sample of the strain Nitrosomonas RST41-3/pEBZ154 was deposited on Apr. 6, 1994, under the terms of the Budapest Treaty with the DSM-Deutsche Sammlung von Mikroorganismen und Zellkulturen GmbH, Mascheroder Weg 16, D-38124 Braunschweig, Germany.

We claim:

1. Bioluminescent nitrifying bacterium Nitrosomonas RST41-3 or a mutant thereof which comprises the plasmid pEBZ175 or the transposon-carrying plasmid pEBZ177.

2. Bioluminescent nitrifying bacterium according to claim 1, which is the strain RST41-3/pEBZ154 according to deposition number DSM 9146.

3. In a sewage treatment process comprising decomposing said sewage by the action of nitrifying bacteria on said sewage, wherein the improvement comprises using as said nitrifying bacteria bioluminescent nitrifying bacteria according to claim 2.

4. In a sewage treatment process comprising decomposing said sewage by the action of nitrifying bacteria on said sewage, wherein the improvement comprises using as said nitrifying bacteria bioluminescent nitrifying bacteria according to claim 1.

5. A method of producing bioluminescent bacteria, said method comprising transferring luciferase DNA or a luciferase-β-galactosidase transcription fusion into ammonia-oxidizing bacteria with the aid of a vector system selected from the group consisting of pEBZ154, pEBZ160, pEBZ175 and pEBZ177.

6. A method according to claim 5 wherein Nitrosomonas strains are used as the ammonia-oxidizing bacteria.

7. A method according to claim 5, wherein the vector system is pEBZ154, which is prepared by a process comprising converting pEBZ110 to pEBZ119, pEBZ119 to pEBZ127, and pEBZ127 to pEBZ154.

8. A method according to claim 5, wherein the vector system is pEBZ160, which is prepared by a process comprising converting pEBZ110 to pEBZ119, pEBZ119 to pEBZ127, and pEBZ127 to pEBZ160.

9. A method according to claim 5, wherein the vector system is pEBZ175, which is prepared by a process comprising converting pEBZ112 to pEBZ144, pEBZ144 to pEBZ173, and pEBZ173 to pEBZ175.

10. A method according to claim 5, wherein the vector system is pEBZ177, which is prepared by a process comprising converting pEBZ140 to pEBZ177.

11. A method according to claim 6, wherein said Nitrosomonas strain is RST41-3.

12. A method according to claim 11, said Nitrosomonas strain is the strain RST41-3/pEBZ154 according to deposition number DSM 9146.

* * * * *

UNITED STATES PATENT AND TRADEMARK OFFICE
CERTIFICATE OF CORRECTION

PATENT NO. : 5,900,362
DATED : May 4, 1999
INVENTOR(S) : Günther Eberz, et al.

It is certified that error appears in the above-identified patent and that said Letters Patent is hereby corrected as shown below:

Title Page [56], Other Publications, Line 24 — Delete "Britton" and substitute --Bitton--

Col. 9, Line 3 — Delete "mutant" and substitute --descendent--
After "comprises" delete "the" and substitute --a--

Col. 9, Line 4 — Delete "pEBZ175 or the transposon-carrying plasmid pEBZ177" and substitute -- selected from the group consisting of pEBZ154, pEBZ160, pEBZ175 and pEBZ177 --.

Signed and Sealed this

Fourteenth Day of December, 1999

Q. TODD DICKINSON

Attest:

Attesting Officer

Acting Commissioner of Patents and Trademarks